United States Patent

Durbut et al.

Patent Number: 5,733,860
Date of Patent: Mar. 31, 1998

[54] ALKYLENE CARBONATED AND THEIR PREPARATION

[75] Inventors: Patrick Durbut, Verviers; Guy Broze, Grace-Hollogne, both of Belgium

[73] Assignee: Colgate-Palmolive Company, Piscataway, N.J.

[21] Appl. No.: 672,000

[22] Filed: Jun. 28, 1996

[51] Int. Cl.[6] .............................. C11D 11/00; C11D 3/60
[52] U.S. Cl. .................. 510/405; 510/108; 510/220; 510/235; 510/405; 510/415
[58] Field of Search .............................. 510/108, 220, 510/235, 405, 415

[56] References Cited

U.S. PATENT DOCUMENTS

| | | | |
|---|---|---|---|
| 2,932,618 | 4/1960 | Oberdorfer et al. | 252/170 |
| 2,991,254 | 7/1961 | Oberdorfer et al. | 252/170 |
| 3,949,149 | 4/1976 | Cherubim et al. | 428/529 |
| 4,508,634 | 4/1985 | Elepano et al. | 252/163 |
| 5,207,838 | 5/1993 | Googin et al. | 134/42 |
| 5,346,640 | 9/1994 | Cassius | 252/162 |

*Primary Examiner*—Yogendra N. Gupta
*Assistant Examiner*—Sabiha N. Qazi
*Attorney, Agent, or Firm*—Richard E. Nanfeldt; James M. Serafino

[57] ABSTRACT

The present invention relates to nitrogen-free amphiphiles which are $C_6$–$C_{14}$ alkylene carbonates and their use in anionic surfactant containing cleaning compositions.

10 Claims, No Drawings

ALKYLENE CARBONATED AND THEIR PREPARATION

FIELD OF THE INVENTION

The present invention relates to nitrogen-free amphiphiles which are $C_6$–$C_{14}$ alkylene carbonates and their use in anionic surfactant containing cleaning compositions.

BACKGROUND OF THE INVENTION

U.S. provisional applications: 60/001,307; 60/001,308 and 60/001,503 are directed to analephotropic mixtures of anionic surfactants with a nitrogen containing surfactant having a high dipole such as N-alkyl-pyrrolidones, coco amidopropyl betaine and amine oxide. Analephotropy pertains to mixtures for which the adsorbed layer at solid-liquid interface has the same composition than in the bulk solution (by analogy with azeotropy for liquid-vapor equilibrium). This behavior arises from attractive interactions taking place between surfactant molecules in the adsorbed layer.

The main interest of analephotropy for practical applications is that a higher surfactant concentration ("surface excess concentration") is made available for detergency at the solid-liquid interface, at a minimum total surfactant concentration versus anionic surfactant alone.

Strictly speaking the larger effect occurs at a well defined proportion of the two surfactants, that varies from one mixture to another. Nevertheless, analephotropy makes surfactant mixtures converge to the most effective adsorbed film, i.e. even in most frequent cases of anionic rich mixtures the composition of the adsorbed layer is not too far from the optimum, and warrants a significant concentration of anionic surfactant at the solid surface.

New nitrogen-free amphiphilic molecules have been prepared and their adsorption properties have been measured in the presence of LAS (Linear Alkylbenzene Sulfonate) anionic surfactant.

Those nitrogen-free molecules are of extreme interest due to the increasing environmental pressure in some countries against nitrogen containing raw materials, linked to the possible presence of nitrosamines.

The present invention relates to $C_{6-14}$ alkylene carbonates and their preparation as well as the use of these $C_6$–$C_{14}$ alkylene carbonates, more preferably $C_8$–$C_{12}$ alkylene carbonates, in anionic surfactant cleaning compositions such as hard surface cleaning composition, wherein analephotropic mixtures are formed between the $C_6$–$C_{14}$ alkylene carbonates and the anionic surfactant in the cleaning composition.

SUMMARY OF THE INVENTION

The present invention relates to alkylene carbonates and their preparation, wherein the alkylene carbonate is depicted by the formula:

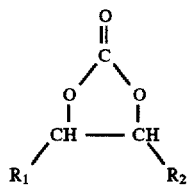

wherein $R_1$ is a $C_n$ alkyl group, $R_2$ is a $C_m$ alkyl group, with n+m being a number from 4 to 12, more preferably from 6 to 10.

The present invention also relates to cleaning compositions such as hard surface cleaning compositions containing analephotropic mixtures of anionic surfactant and the $C_6$–$C_{14}$ alkylene carbonate, wherein the hard surface cleaning composition can be a light duty liquid composition, an all purpose liquid cleaning composition or a microemulsion cleaning composition.

DETAILED DESCRIPTION OF THE INVENTION

The present invention relates to $C_6$–$C_{14}$ alkylene carbonates and their preparation as well as to use of these $C_6$–$C_{14}$ alkylene carbonates in conjunction with anionic surfactants as analephotropic mixtures in hard surface cleaning compositions such as light duty cleaning compositions, all purpose cleaning compositions and microemulsion cleaning compositions, wherein these hard surface cleaning compositions do not contain any inorganic builders or any nitrogen containing surfactants.

The $C_6$–$C_{14}$ alkylene carbonates are depicted by the structure:

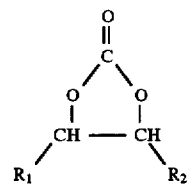

wherein $R_1$ is a $C_n$ alkyl group, $R_2$ is H or is a $C_m$ alkyl group, with n+m being a number from 4 to 12, more preferably from 6 to 10, such as 1-octene carbonate or 1-dodecene carbonate. The $C_6$–$C_{14}$ alkylene carbonate is prepared by the reaction of alkane alpha-diol with phosgene as depicted by the following:

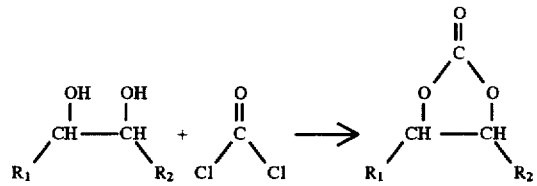

wherein $R_1$ is a $C_n$ alkyl group, with n being a number from 4 to 12 and $R_2$ is a $C_m$ alkyl group, with n+m being a number from 4 to 12. The alkane alpha-diols are prepared from the epoxidation of an internal or an alpha-olefin and the subsequent hydrolysis of the epoxide. The $C_6$–$C_{14}$ alkylene carbonate can also be prepared by a another synthesis route by the reaction of molecular oxygen $O_2$ on the said internal or alpha-olefin to form the epoxide as intermediate product, followed by the direct reaction of carbon dioxide $CO_2$ on the epoxide in appropriate conditions, as depicted by the following:

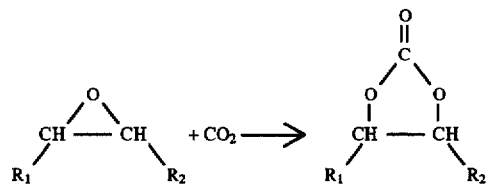

The $C_6$–$C_{14}$ alkylene carbonates are nitrogen-free amphiphiles having a high dipole moment. The beneficial impact of the presence of the permanent dipole moment of the $C_6-C_{14}$ alkylene carbonate, that leads to attractive interactions between the alkylene carbonate and anionic surfactants and leads to analephotropic mixtures of the two types of amphiphiles, could be further enhanced by grafting a hydrophilic moiety to the alkylene carbonate. The light duty liquid compositions containing the $C_6-C_{14}$ alkylene carbonate comprise approximately by weight:

(a) 0.5% to 40% of at least one anionic surfactant;

(b) 0.3% to 10% of a $C_6-C_{14}$ alkylene carbonate;

(c) 0 to 10% of a nonionic surfactant;

(d) 0 to 10% of a solubilizer; and (e) balance being water.

The all purpose cleaning compositions containing the $C_6-C_{14}$ alkylene carbonate comprise approximately by weight:

(a) 0.5% to 15% of at least one anionic surfactant;

(b) 0.3% to 10% of a $C_6-C_{14}$ alkylene carbonate;

(c) 0 to 8% of a nonionic surfactant;

(d) 0 to 20% of a cosurfactant;

(e) 0 to 0.4% of a perfume; and (f) balance being water.

The microemulsion cleaning composition containing the $C_6-C_{14}$ alkylene carbonate comprises approximately by weight:

(a) 0.5% to 15% of at least one anionic surfactant;

(b) 0.3% to 10% of a $C_6-C_{14}$ alkylene carbonate;

(c) 0 to 8% of a nonionic surfactant;

(d) 1% to 20% of a cosurfactant;

(e) 0.4% to 10% of a perfume, water insoluble hydrocarbon or essential oil; and (f) balance being water.

A thickened hard surface having a dynamic viscosity of at least about 8.000 Pas, more preferably at least about 12.000 Pas comprises approximately by weight:

(a) 8% to 10% of an anionic surfactant such as sodium lauryl sulfate;

(b) 0.1% to 8% of an electrolyte such as sodium chloride;

(c) 0.5% to 5% of a $C_6-C_{14}$ alkylene carbonate; and (d) the balance being water.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc. The instant compositions show a marked improvement in ecotoxicity as compared to existing commercial products.

The hydrocarbon such as a perfume is present in the dilute o/w microemulsion in an amount of from 0.1% to 10% by weight, preferably from 0.4% to 6.0% by weight, especially preferably from 0.5% to 3.0% by weight, such as weight percent. If the amount of hydrocarbon (perfume) is less than 0.4% by weight it becomes more difficult to form the o/w microemulsion. If the hydrocarbon (perfume) is added in amounts more than 10% by weight, the cost is increased without any additional cleaning benefit and, in fact, with some diminishing of cleaning performance insofar as the total amount of greasy or oily soil which can be taken up in the oil phase of the microemulsion will decrease proportionately.

Furthermore, although superior grease removal performance will be achieved for perfume compositions not containing any terpene solvents, it is apparently difficult for perfumers to formulate sufficiently inexpensive perfume compositions for products of this type (i.e., very cost sensitive consumer-type products) which includes less than 20%, usually less than 30%, of such terpene solvents.

Thus, merely as a practical matter, based on economic consideration, the dilute o/w microemulsion detergent cleaning compositions of the present invention may often include as much as 0.2% to 7% by weight, based on the total composition, of terpene solvents introduced thereunto via the perfume component. However, even when the amount of terpene solvent in the cleaning formulation is less than 1.5% by weight, such as up to 0.6% by weight or 0.4% by weight or less, satisfactory grease removal and oil removal capacity is provided by the inventive diluted o/w microemulsions.

Thus, for a typical formulation of a diluted o/w microemulsion according to this invention a 20 milliliter sample of o/w microemulsion containing 1% by weight of perfume will be able to solubilize, for example, up to 2 to 3 ml of greasy and/or oily soil, while retaining its form as a microemulsion, regardless of whether the perfume contains 0%, 0.1%, 0.2%, 0.3%, 0.4%, 0.5%, 0.6%, 0.7% or 0.8% by weight of terpene solvent. In other words, it is an essential feature of the compositions of this invention that grease removal is a function of the result of the microemulsion, per se, and not of the presence or absence in the microemulsion of a "greasy soil removal" type of solvent.

In place of the perfume one can employ a water insoluble paraffin or isoparaffin having 6 to 18 carbon or an essential oil.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen.

Regarding the anionic surfactant present in the light duty liquid all purpose cleaning or microemulsion compositions any of the conventionally used water-soluble anionic surfactants or mixtures of said anionic detergents and anionic detergents can be used in this invention. As used herein the term "anionic surfactant" is intended to refer to the class of anionic and mixed anionic-nonionic surfactants providing detersive action.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble surfactant. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an alpha-olefin.

Other examples of suitable anionic sulfonate surfactants are the paraffin sulfonates containing 10 to 20, preferably 13 to 17, carbon atoms. Primary paraffin sulfonates are made by reacting long-chain alpha-olefins and bisulfites and paraffin sulfonates having the sulfonate group distributed along the paraffin chain are shown in U.S. Pat. Nos. 2,503,280; 2,507,088; 3,260,744; 3,372,188; and German Patent 735, 096.

Examples of satisfactory anionic sulfate surfactants are the $C_8$–$C_{18}$ alkyl sulfate salts and the $C_8$–$C_{18}$ alkyl sulfate salts and the $C_8$–$C_{18}$ alkyl ether polyethenoxy sulfate salts having the formula $R(OC_2H_4)_n OSO_3M$ wherein n is 1 to 12, preferably 1 to 5, and M is a solubilizing cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These detergents can be prepared by reacting an alkyl phenol with 2 to 6 moles of ethylene oxide and sulfating and neutralizing the resultant ethoxylated alkylphenol.

Obviously, these anionic surfactants will be present either in acid form or salt form depending upon the pH of the final composition, with salt forming cation being the same as for the other anionic detergents.

Of the foregoing non-soap anionic surfactants, the preferred surfactants are the $C_9$–$C_{15}$ linear alkylbenzene sulfonates and the $C_{13}$–$C_{17}$ paraffin or alkane sulfonates. Particularly, preferred compounds are sodium $C_{10}$–$C_{13}$ alkylbenzene sulfonate and sodium $C_{13}$–$C_{17}$ alkane sulfonate.

The water soluble nonionic surfactants utilized in this invention are commercially well known and include the primary aliphatic alcohol ethoxylates, secondary aliphatic alcohol ethoxylates, alkylphenol ethoxylates and ethyleneoxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethylenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9-C_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of about 8–15 and give good O/W emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}-C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of dinonyl phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described shampoo. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

The cosurfactant used in the all purpose cleaning or microemulsion composition may play an essential role in the formation of the all purpose cleaning composition or microemulsion composition. Three major classes of compounds have been found to provide highly suitable cosurfactants for the microemulsion over temperature ranges extending from 4° C. to 43° C. for instance; (1) water-soluble $C_3-C_4$ alkanols, polypropylene glycol of the formula $HO(CH_3CHCH_2O)_nH$ wherein n is a number from 2 to 18 and monoalkyl ethers and esters of ethylene glycol and propylene glycol having L. the structural formulas $R(X)_nOH$ and $R_1(X)_nOH$ wherein R is $C_1-C_6$ alkyl, $R_1$ is $C_2-C_4$ acyl group, X is $(OCH_2CH_2)$ or $(OCH_2(CH_3)CH)$ and n is a number from 1 to 4; (2) aliphatic mono- and di-carboxylic acids containing 2 to 10 carbon atoms, preferably 3 to 6 carbons in the molecule; and (3) triethyl phosphate. Additionally, mixtures of two or more of the four classes of cosurfactant compounds may be employed where specific pH's are desired.

When the mono- and di-carboxylic acid (Class 2) cosurfactants are employed in the instant compositions at a concentration of 2 to 10 wt. %, the microemulsion compositions can be used as a cleaners for bathtubs and other hard surfaced items, which are acid resistant thereby removing lime scale, soap scum and greasy soil from the surfaces of such items damaging such surfaces. If these surfaces are of zirconium white enamel, they can be damaged by these compositions.

An aminoalkylene phosphonic acid at a concentration of 0.01 to 0.2 wt. % can be optionally used in conjunction with the mono- and di-carboxylic acids, wherein the aminoalkylene phosphonic acid helps prevent damage to zirconium white enamel surfaces. Additionally, 0.05 to 1% of phosphoric acid can be used in the composition.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, mono, di, tri propylene glycol mono methyl ether, tetraethylene glycol monobutyl ether, propylene glycol tertiary butyl ether, ethylene glycol monoacetate and dipropylene glycol propionate.

Representative members of the aliphatic carboxylic acids include $C_3-C_6$ alkyl and alkenyl monobasic acids and dibasic acids such as glutaric acid and mixtures of glutaric acid with adipic acid and succinic acid, as well as mixtures of the foregoing acids as well as acrylic acid or propionic acid.

While all of the aforementioned glycol ether compounds and acid compounds provide the described stability, the most preferred cosurfactant compounds of each type, on the basis of cost and cosmetic appearance (particularly odor), are diethylene glycol monobutyl ether and a mixture of adipic, glutaric and succinic acids, respectively. The ratio of acids in the foregoing mixture is not particularly critical and can be modified to provide the desired odor. Generally, to maximize water solubility of the acid mixture glutaric acid, the most water-soluble of these three saturated aliphatic dibasic acids, will be used as the major component.

Generally, weight ratios of adipic acid:glutaric acid:succinic acid is 1-3:1-8:1-5, preferably 1-2:1-6:1-3, such as 1:1:1, 1:2:1, 2:2:1, 1:2:1.5, 1:2:2, 2:3:2, etc. can be used with equally good results.

Still other classes of cosurfactant compounds providing stable microemulsion compositions at low and elevated temperatures are the mono-, di- and triethyl esters of phosphoric acid such as triethyl phosphate.

The amount of cosurfactant required to stabilize the microemulsion compositions will, of course, depend on such factors as the surface tension characteristics of the cosurfactant the type and amounts of the primary surfactants and perfumes, and the type and amounts of any other additional ingredients which may be present in the composition and which have an influence on the thermodynamic factors enumerated above. Generally, amounts of cosurfactant in the range of from 0% to 50%, preferably from 0.5% to 15%, especially preferably from 1% to 7%, by weight provide stable dilute o/w microemulsions for the above-described levels of primary surfactants and perfume and any other additional ingredients as described below.

As will be appreciated by the practitioner, the pH of the final all purpose cleaning composition or microemulsion composition will be dependent upon the identity of the cosurfactant compound, with the choice of the cosurfactant being effected by cost and cosmetic properties, particularly odor. For example, microemulsion compositions which have a pH in the range of 1 to 10 may employ either the class 1 or the class 4 cosurfactant as the sole cosurfactant, but the pH range is reduced to 1 to 8.5 when the polyvalent metal salt is present. On the other hand, the class 2 cosurfactant can only be used as the sole cosurfactant where the product pH is below 3.2. However, where the acidic cosurfactants are employed in admixture with a glycol ether cosurfactant, compositions can be formulated at a substantially neutral pH (e.g., pH 7±1.5, preferably 7±0.2).

The ability to formulate neutral and acidic products without builders which have grease removal capacities is a feature of the present invention because the prior art o/w microemulsion formulations most usually are highly alkaline or highly built or both.

In addition to their excellent capacity for cleaning greasy and oily soils, the low pH o/w microemulsion formulations also exhibit excellent cleaning performance and removal of soap scum and lime scale in neat (undiluted) as well as in diluted usage.

Because the compositions as prepared are aqueous liquid formulations and since no particular mixing is required to form the o/w microemulsion, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The instant formulas explicitly exclude alkali metal silicates and alkali metal builders such as alkali metal polyphosphates, alkali metal carbonates, alkali metal phosphonates and alkali metal citrates because these materials, if used in the instant composition, would cause the composition to have a high pH as well as leaving residue on the surface being cleaned.

In addition to the above-described essential ingredients required for the formation of the instant all purpose cleaning or microemulsion composition, the compositions of this invention may often and preferably do contain one or more additional ingredients which serve to improve overall product performance.

One such ingredient is an inorganic or organic salt or oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level. Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalence between the anionic surfactant and the multivalent metal cation. For example, for each gram-ion of $Mg^{++}$ there will be 2 gram moles of paraffin sulfonate, alkylbenzene sulfonate, etc., while for each gram-ion of $Al^{3+}$ there will be 3 gram moles of anionic surfactant. Thus, the proportion of the multivalent salt generally will be selected so that one equivalent of compound will neutralize from 0.1 to 1.5 equivalents, preferably 0.9 to 1.4 equivalents, of the acid form of the anionic surfactant.

At higher concentrations of anionic surfactant, the amount of multivalent salt will be in range of 0.5 to 1 equivalents per equivalent of anionic surfactant.

The instant compositions can include from 0% to 2.5%, preferably from 0.1% to 2.0% by weight of the composition of a $C_8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt % of the fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The instant all purpose cleaning or microemulsion composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-bromo-5-nitro-dioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

The essential ingredients in the light duty liquid composition can be solubilized in one preferred embodiment of the invention in an aqueous medium comprising water and a mixture of an alkyl monoethanol amides such as $C_{12}$–$C_{14}$ alkyl monoethanol amide (LMMEA) at a concentration of 1 to 4 wt. %, and an alkyl diethanol amides such as coco diethanol amide (CDEA) or lauryl diethanol amide (LDEA) at a concentration of 1 to 4 wt. % wherein the ratio of monoethanol amide to diethanol amide is about 3:1 to about 1:3. A composition made with only alkyl diethanol amide has inferior grease removal ability, corn oil emulsification and foam properties as compared to the commercial Palmolive™ LDL which is being currently sold on the market. A composition made with only alkyl monoethanol amide and no alkyl diethanol amide is not as optically clear as a composition made with both alkyl monoethanol amide and alkyl diethanolamide. Formulas containing only the alkyl monoethanol amide are unstable and becomes turbid. This is critical because during shipping and storage the temperature can be low and the composition must be stable at these lower temperatures.

Less preferred solubilizing agents are $C_2$–$C_3$ mono and di-hydroxy alkanols, e.g., ethanol, isopropanol and propylene glycol. Suitable water soluble hydrotropic salts include sodium, potassium, ammonium and mono-, di- and triethanolammonium salts. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from about 1% to 15%, preferably 2% to 12%, most preferably 3%–8%, by weight of the detergent composition with the proportion of ethanol, when present, being 5% of weight or less in order to provide a composition having a flash point above about 46° C. Preferably the solubilizing ingredient will be a mixture of ethanol and a water soluble salt of a $C_1$–$C_3$ substituted benzene sulfonate hydrotrope such as sodium xylene sulfonate or sodium cumene sulfonate or a mixture of said sulfonates or ethanol and urea. Inorganic alkali metal or alkaline earth metal salts such as sodium sulfate, magnesium sulfate, sodium chloride and sodium citrate can be added at concentrations of 0.5 to 4.0 wt. % to modify the cloud point of the nonionic surfactant and thereby control the haze of the resultant solution. Various other ingredients such as urea at a concentration of about 0.5 to 4.0 wt. % or urea at the same concentration in combination with ethanol at a concentration of about 0.5 to 4.0 wt. % can be used as solubilizing agents. Other ingredients which have been added to the compositions at concentrations of about 0.1 to 4.0 wt. percent are perfumes, preservatives, color stabilizers, sodium bisulfite, ETDA, and proteins such as lexine protein. One to 4 wt. % of an alkali metal salt of isethionic acid having the formula $CH_2OHCHSO_3H$ can be used in the amide free formula of the instant composition as a substitute for the amide as a solubilizing agent.

The foregoing solubilizing ingredients also facilitate the manufacture of the inventive compositions because they tend to inhibit gel formation.

In addition to the previously mentioned essential and optional constituents of the light duty liquid detergent, one may also employ normal and conventional adjuvants, provided they do not adversely affect the properties of the detergent. Thus, there may be used various coloring agents and perfumes; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be about 0.1 to 5% by weight and preferably less than about 2% by weight. Sodium bisulfite can be used as a color stabilizer at a concentration of about 0.01 to 0.2 wt. %. Typical preservatives are dibromodicyano-butane, citric acid, benzylic alcohol and poly (hexamethylene-biguamide) hydrochloride and mixtures thereof.

The instant light duty liquid compositions can contain about 0.1 to about 4 wt. percent, more preferably 0.5 to 3 wt. percent of an alkyl polysaccharide surfactant. The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2-, 3-, or 4- positions rather than at the 1-position, (thus giving e.g. a glucosyl or galactosyl as opposed to a glucoside or galactoside). However, attachment through the 1-position, i.e., glucosides, galactoside, fructosides, etc., is preferred. In the preferred product the additional saccharide units are predominately attached to the previous saccharide unit's 2-position. Attachment through the 3-, 4-, and 6-positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

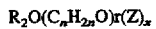

$R_2O(C_nH_{2n}O)r(Z)_x$ wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than 50%, preferably less than 10%, more preferably less than about 5%, most preferably 0% of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, PA. APG25 is a nonionic alkyl polyglycoside characterized by the formula:

$C_nH_{2n+1}O(C_6H_{10}O_5)_xH$ wherein n=10 (2%); n=122 (65%); n=14 (21–28%); n=16 (4–8%) and n=18 (0.5%) and x (degree of polymerization) =1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The following examples which are made by simple mixing at 25° C. are in wt. % unless otherwise expressed.

EXAMPLE I

Preparation of Cyclic Alkylene Carbonates

The preparation of cyclic carbonate derivatives of 1,2-alkanediols is illustrated by the synthesis of 4-decyl-1,3-dioxolan-2-one (1,2-dodecanediol cyclic carbonate, or 1-dodecene carbonate) (M.W. 228.3). Raw materials have been used as received from Aldrich Chemical Co. A cooled 20% solution of 0.178 mole of phosgene (1.2 equivalents) in a second aromatic solvent such as toluene was added dropwise with stirring to a cooled solution of 30.0 g. (0.148 mole) of 1,2-dodecane diol and 35.9 g. (2.4 equivalents) of triethylamine in 100 ml of a first aromatic solvent such as dried toluene in a 500 ml two-necked round-bottomed flask equipped with a condenser and a CaCl2 tube, at such a rate that the temperature was maintained at −5° to 0° C., by means of an ice-acetone bath. The mixture was then allowed to go back to room temperature, and the reaction continued overnight at this temperature. The mixture was then filtered and the filtrate was evaporated under vacuum. The crude product was distilled (120°–180° C./reduced pressure), giving a clear, colorless liquid. Yield is about 80%. Residue was attributed to the formation of cyclic oligomeric/polymeric materials and has not been further characterized. Purity of isolated cyclic alkylene carbonate is at least 98% according to classical analysis (RMH $^1H$, $^{13}C$, Mass Spectrometry, IR and GC). The same procedure was applied to prepare 1-decene carbonate (M.W. 200.3) and 1-octene carbonate (M.W. 172.2) from 1,2-decanediol and 1,2-octanediol, respectively.

EXAMPLE II

Adsorption behavior and surface tension measurements were made for a sodium salt linear $C_{8-16}$ alkyl benzene sulfonate and $C_8$ alkylene carbonate and $C_{12}$ alkylene carbonate at various molar ratios.

Adsorption Behavior at Water-Air Interface of LAS-CxAKC Mixtures

| LAS/CxAKC molar ratios | $C_{50}$ concentrations C8AKC | | $C_{50}$ concentrations C12AKC | |
|---|---|---|---|---|
| | g/l | mol/l | g/l | mol/l |
| 1/0 | 0.039 | 115 | 0.039 | 115 |
| 7/1 | 0.024 | 76 | 0.01 | 31 |
| 3/1 | 0.023 | 81 | — | — |
| 2/1 | 0.024 | 85 | — | — |
| 1.1/1 | 0.024 | 93 | — | — |

The $C_{50}$ molar concentration of LAS/$C_8$AKC mix goes through a minimum at a 7/1 proportion. The $C_{50}$ molar concentration is the required minimum total surfactant concentration to lower the surface tension of water to 50 mN/m. This profile evidences analephotropy between LAS and alkylene carbonate, and results from strong attractive interactions between molecules in adsorbed layer. At the curve minimum, the composition at the water-air interface is the same as in the solution. It means that the analephotropic composition is very rich in the least expensive material: LAS.

As a practical consequence, the adsorption of LAS is strongly enhanced and it is the main component present at the water-air interface. The mixed adsorbed layer contains a proportion of about 88% LAS. It is much larger than the value of 12% observed with LAS/$C_{9-11}$E5 system at same molar ratio.

A further proof of analephotropy is that the LAS content in adsorbed layer composition should be larger for higher proportions in alkylene carbonate in the bulk solution than with LAS/$C_8$AKC 7/1 composition, i.e. for compositions located on the left side of the 7/1 ratio defined as the analephotropic, on a scale going from pure $C_8$AKC to pure LAS, with all possible LAS/$C_8$AKC molar proportions in-between.

Surface Tension as a Function of Concentration of
$C_8AKC$ at Constant LAS Concentration

| Molar ratio of LAS | LAS Weight Ratio | Conc LAS (g/l) | Conc C8AKC (mg/l) | Total Conc (g/l) | Surface Tension (mN/m) |
|---|---|---|---|---|---|
| 2/1 (0.67) | 0.79 | 0.020 | 5.2 | 0.025 | 50.0 |
| 3/1 (0.75) | 0.86 | 0.020 | 3.3 | 0.023 | 50.8 |
| 1/0.9 (0.53) | 0.71 | 0.020 | 8.2 | 0.028 | 48.7 |
| 7/1 (0.875) | 0.93 | 0.020 | 1.4 | 0.021 | 51.7 |

Surface Tension as a Function of Concentration of
LAS at Constant $C_8AKC$ Concentration

| Molar ratio of C8AKC | C8AKC Wt. Ratio | Conc C8AKC (mg/l) | Conc LAS (g/l) | Total Conc (g/l) | Surface Tension (mN/m) |
|---|---|---|---|---|---|
| 2/1 (0.33) | 0.21 | 5.2 | 0.02 | 0.025 | 50.0 |
| 3/1 (0.25) | 0.145 | 5.2 | 0.031 | 0.036 | 47.2 |
| 1/0.9 (0.47) | 0.29 | 5.2 | 0.012 | 0.017 | 52.8 |
| 7/1 (0.125) | 0.068 | 5.2 | 0.071 | 0.076 | 42.1 |

From the surface tension data it can be calculated that the adsorbed layer contains a molar portion of 73% LAS and 27% of $C_8$ alkylene carbonate.

At water-air interface only 12% $C_8AKC$ are required to adsorb a maximum LAS (88%) at a minimum surfactant concentration. The total surfactant concentration needed to reduce the surface tension to 50 mN/m ($C_{50}$) is reduced by a factor of 1.5 with 7/1 LAS/$C_8AKC$ analephotropic composition versus LAS alone.

Higher $C_8AKC$ proportions allow to enrich the adsorbed layer in LAS, but at higher $C_{50}$ concentrations. With 2/1 LAS/$C_8AKC$ system the LAS content is 73% versus 67% in bulk. Moreover a larger amount of surfactant is delivered (3.4 micromol/$m^2$) than with LAS alone (2.8 micromol/$m^2$), due to a tighter packing of molecules.

Effects are maximized with the more hydrophobic $C_{12}AKC$. Even less surfactants are needed versus LAS (3.7 time less), but still adsorbing a majority of LAS (88%).

At water-solid grease interface LAS/$C_{12}AKC$ system shows analephotropy at same 7/1 ratio as observed at air interface, though effects are less pronounced. The $C_{10}$ concentration is 1.7 times lower than LAS. The $C_{10}$ concentration is defined as the minimum total surfactant concentration required to deliver an adhesion tension of 10 mN/m at the interface between said surfactant aqueous solution and a flat layer of solid grease (glycerol tripalmitate). The adhesion tension is defined as the net force exerted by a liquid on a liquid at the wetting line and depends upon the contact angle θ which the liquid makes on the solid substrate at the equilibrium. The adhesion tension is defined as the cosine of the contact angle θ that the liquid composition makes with the substrate times the surface tension of the liquid composition $\gamma_L$ as measured at 25° C. on a weakly polar solid substrate which is glycerol tripalmitate.

LAS/$C_{12}AKC$ 7% compositions deliver outstanding performance in oily-particulate soil removal test, in line with prediction of enhanced LAS anionic surfactant adsorption.

EXAMPLE III

In the kaolin particulate soil test the ability of products to remove a mixture of oil and kaolin from a solid surface is gauged in static conditions at room temperature. Clean glass slides as used for microscopy are soiled by soaking in a mixture of oil and particulate soil in a 100 ml beaker. Soil composition is 70g mineral oil (Esso SAE 15W multigrade motor oil), 35g particulate soil (kaolin), and 35g tetrachloroethylene (removed in oven at 80° C.). Kaolin is medium particle size china clay from ECC International (grade E powder—65% minimum below 10 microns, with 0.05% maximum above 53 microns).

Each slide is numbered and weighted (A) on an analytical balance (0.1 mg) before the soiling operation. The glass slides are soiled up to about ¾ of their full length, and extra soil at the slide edge allowed to drop in the beaker. Sets of six slides per product are prepared. All the soiled slides (36 for 6 products) are hanged with small pincers on a specially lab designed device.

The whole set of slides is allowed to dry in an oven at 80° C. for 1 hour, so as to remove the carrier (tetrachloroethylene). All the slides are allowed to cool down to room temperature for 2 hours. Extra amounts of oily soil that has drained at the bottom of each slide are then gently removed with a paper towel. Each soiled slide is weighted again (B) and amount of deposited soil per slide calculated (B-A). Afterwards all soiled slides are randomized to obtain about the same weight of soil that each product will see on average. In practice, when the mean weights of soil on each set of six slides are calculated, only a few slides are needed to be exchanged through the whole set so as to achieve about the same average soil amount and the same weight distribution for each product. As a consequence this randomization step is not really time consuming. This protocol has been proven useful to minimize as much as possible the final result standard deviation.

The soiled slides are then soaked one by one for 15 minutes at RT in 100 ml neat compositions, and carefully rinsed afterwards with tap water. Regarding test reproducibility and reliability this step is the most critical to provide the right rinsing without removing the remaining soil. After drying in the oven for 45 minutes at 50° C., and cooling down at RT for 30 minutes, the washed slides are weighted (C). Soil removal percentages are calculated from the weight loss: [(B-C)/(B-A)]×100, and standard deviations calculated. In general lower values than 5% are obtained for the standard deviations. Reported results are means of 6 slides.

The kaolin particulate soil allows to discriminate different cleaning compositions.

LAS/$C_{12}$alkylene carbonate combination delivers uttermost cleaning performance, at 7/3 ratio. To achieve such a ratio, we added DPM (dipropylene glycol mono methyl ether) to help solubilize 1-dodecene carbonate.

Three products were compared: Ajax Regular, LAS/$C_{12}$ alkylene carbonate (7:1) and LAS/$C_{12}$ alkylene carbonate (7:3). Ajax Regular exhibited 42% soil removal while LAS/$C_{12}$ alkylene carbonate at 7:1 ratio exhibited 78% soil removal and at a 7:3 ratio exhibited 98% soil removal.

The compositions are:

|  | LAS/C12AKC 7/1 | LAS/C12AKC 7/3 | Ajax Regular |
|---|---|---|---|
| NaLAS (52%) | 6.38 | 5.43 |  |
| C12alkylene carbonate | 0.62 | 1.57 |  |

|                              | LAS/C12AKC 7/1 | LAS/C12AKC 7/3 | Ajax Regular |
|------------------------------|----------------|----------------|--------------|
| Dipropylene glycol mono methyl ether | —      | 3.5            |              |
| Water                        | Balance        | Balance        | Balance      |

EXAMPLE IV

The following compositions were prepared by simple mixing at 25° C.

|                          | A    | B      |
|--------------------------|------|--------|
| Sodium lauryl sulfonate  | 12   | 12     |
| $C_{12}$ alkylene carbonate |   | 1.2    |
| Sodium chloride          | 3    | 3      |
| Water                    | Bal. | Bal.   |
| Dynamic viscosity (Pas)  | 250  | 16,000 |

EXAMPLE V

The following light duty liquid composition containing a total concentration of 34% of surfactants was prepared by simple mixing at 25° C., and was found performing.

|                                             | %    |
|---------------------------------------------|------|
| Sodium paraffin sulfonate $C_{14}$—$C_{17}$ (60%) | 25.5 |
| Alcohol ether sulfate 2EO                   | 8.5  |
| $C_{10}$ alkylene carbonate                 | 5.0  |
| Dipropylene glycol monomethyl ether         | 5.0  |
| Ethanol                                     | 2.5  |
| Water                                       | Bal. |

What is claimed is:

1. A thickened aqueous composition comprising approximately by weight:
   (a) 8% to 20% of an anionic surfactant;
   (b) 0.5% to 5.0% of a $C_{11}$–$C_{14}$ alkylene carbonate, of formula

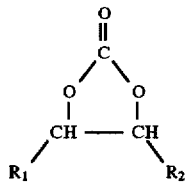

wherein $R_1$ is a $C_n$ alkyl group, $R_2$ is H or is a $C_m$ alkyl group, with n+m being a number from 11–14;

(c) 0.1% to 8% of an electrolyte; and
   (d) the balance being water.

2. A cleaning composition comprising approximately by weight:
   (a) 0.5% to 40% of at least one anionic surfactant;
   (b) 0.3% to 10% of a $C_6$–$C_{14}$ alkylene carbonate; and
   (c) the balance being water.

3. A cleaning composition according to claim 2, further including 0 to 10 wt. % of a nonionic surfactant.

4. A cleaning composition according to claim 3 further including 0 to 10 wt. % of a solubilizer.

5. A cleaning composition according to claim 3 wherein the concentration of the anionic surfactant is 0.5 wt. % to 15 wt. %.

6. A cleaning composition according to claim 5 further including 0 to 20 wt. % of a cosurfactant.

7. A cleaning composition according to claim 6 further including 0 to 0.4 wt. % of a perfume.

8. A cleaning composition according to claim 3 further including 1 wt. % to 20 wt. % of a cosurfactant.

9. A cleaning composition according to claim 8 further including 0.4 wt. % to 10 wt. % of a water insoluble compound selected from the group of perfumes, essential oils or water insoluble hydrocarbons.

10. A process for preparing an alkylene carbonate having the structure of:

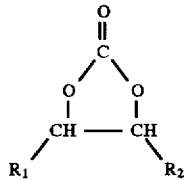

wherein $R_1$ is a $C_n$ alkyl group, $R_2$ is H or is a $C_m$ alkyl group, with n+m being a number from 11 to 14 which comprises the step of reacting 0° C. to –5° C. a solution of triethylamine and an alkane diol having the structure of:

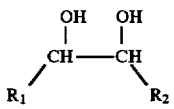

wherein $R_1$ is a $C_n$ alkyl group, $R_2$ is H or is a $C_m$ alkyl group, with n+m being a number from 4 to 12 dissolved in a first aromatic solvent with phosgene dissolved in a second aromatic solvent and subsequently allowing the reaction mixture to warm to room temperature.

* * * * *

UNITED STATES PATENT AND TRADEMARK OFFICE
CERTIFICATE OF CORRECTION

PATENT NO. : 5,733,860
DATED : March 31, 1998
INVENTOR(S) : Durbut et al

It is certified that error appears in the above-indentified patent and that said Letters Patent is hereby corrected as shown below:

On the title page: Item [54] and Column 1, line 2,

Title should read "Alkylene Carbonates and Their Preparation"

Signed and Sealed this

Twenty-third Day of June, 1998

Attest:

BRUCE LEHMAN

Attesting Officer     Commissioner of Patents and Trademarks